United States Patent
Zaveri

(10) Patent No.: US 9,517,212 B1
(45) Date of Patent: Dec. 13, 2016

(54) MEDICATED ADHESIVE PAD ARRANGEMENT

(71) Applicant: Chandra Zaveri, Rancho Palos Verdes, CA (US)

(72) Inventor: Chandra Zaveri, Rancho Palos Verdes, CA (US)

(*) Notice: Subject to any disclaimer, the term of this patent is extended or adjusted under 35 U.S.C. 154(b) by 224 days.

(21) Appl. No.: 13/694,272

(22) Filed: Nov. 15, 2012

(51) Int. Cl.
| | |
|---|---|
| A61F 13/00 | (2006.01) |
| A61K 9/70 | (2006.01) |
| A61K 47/32 | (2006.01) |
| A61K 33/30 | (2006.01) |
| A61K 31/60 | (2006.01) |
| A61K 47/10 | (2006.01) |
| A61F 13/02 | (2006.01) |

(52) U.S. Cl.
CPC ......... *A61K 9/7061* (2013.01); *A61F 13/0276* (2013.01); *A61K 9/7084* (2013.01); *A61K 31/60* (2013.01); *A61K 33/30* (2013.01); *A61K 47/10* (2013.01); *A61K 47/32* (2013.01); *A61F 2013/0296* (2013.01)

(58) Field of Classification Search
USPC ............................................ 602/48; 128/894
See application file for complete search history.

(56) References Cited

U.S. PATENT DOCUMENTS

| | | | | |
|---|---|---|---|---|
| 1,863,122 A | * | 6/1932 | Matthews | B65D 7/24 220/327 |
| 1,955,918 A | * | 4/1934 | Jung, Jr. | A61F 13/063 128/894 |
| 2,015,497 A | * | 9/1935 | Scholl | A61F 13/063 128/894 |
| 3,063,448 A | * | 11/1962 | Scholl | A61F 13/063 128/894 |
| 3,063,555 A | * | 11/1962 | Hanington | A61F 13/063 128/894 |
| 3,741,210 A | * | 6/1973 | Johnston | A61F 13/063 128/894 |
| 4,117,841 A | | 10/1978 | Perrotta et al. | |
| 5,147,338 A | | 9/1992 | Lang et al. | |
| 5,242,433 A | * | 9/1993 | Smith | A61K 8/0208 401/132 |
| 5,254,109 A | * | 10/1993 | Smith | A61F 15/001 401/132 |
| D363,126 S | | 10/1995 | Dusek | |
| 5,538,732 A | * | 7/1996 | Smith | A61K 8/0208 424/402 |
| 6,001,380 A | * | 12/1999 | Smith | A61K 8/0208 424/402 |
| 6,106,818 A | * | 8/2000 | Dulog | A61K 8/0208 424/401 |
| 6,190,698 B1 | * | 2/2001 | Cochran | A61K 9/2846 424/480 |
| 6,303,140 B1 | | 10/2001 | Dever et al. | |
| 8,597,667 B2 | * | 12/2013 | Mou | A45D 34/04 424/401 |
| 2004/0039323 A1 | * | 2/2004 | Utsugi | A61F 13/023 602/48 |

(Continued)

*Primary Examiner* — Kim M Lewis
(74) *Attorney, Agent, or Firm* — Don Finkelstein

(57) ABSTRACT

A medicated pad which may be removably placed over a skin disorder such as acne to provide a relatively rapid treatment for relieving such skin disorder and may then be easily removed from the person.

17 Claims, 1 Drawing Sheet

(56) References Cited

U.S. PATENT DOCUMENTS

| | | | | |
|---|---|---|---|---|
| 2005/0233003 A1* | 10/2005 | Goldshtein | .......... | A61K 9/5138 424/490 |
| 2007/0224153 A1* | 9/2007 | LiBrizzi | ................ | A61K 8/368 424/74 |
| 2009/0234308 A1* | 9/2009 | Jackson | ............... | A61K 9/7053 604/307 |
| 2013/0123678 A1* | 5/2013 | Carty | ................. | A61F 13/0253 602/54 |
| 2013/0184663 A1* | 7/2013 | Takada | .............. | A61F 13/00063 604/307 |

* cited by examiner

MEDICATED ADHESIVE PAD ARRANGEMENT

BACKGROUND OF THE INVENTION

Field of the Invention

This invention relates to the medical arts and more; particularly to a medicated adhesive pad for treating acne and/or other similar skin conditions.

Description of the Prior Art

Medicated patches or bandages for treating various conditions on the surface of the skin are well know in the prior art. Such patches are often based on salicylic acid containing plasters as the active ingredient and are widely utilized in a number of corn removers, callus removers, and wart removers sold over the counter. However, there has not heretofore been provided a medicated adhesive patch for adhering to the surface of the skin to treat acne and/or other similar skin conditions which have been successful in providing fast and effective relief to the particular skin area, such as the face of a person, wherein the acne or similar skin conditions may often occur.

In many adolescents, the sudden appearance of an acne "pimple" or other manifestation of this disease has often occurred at times when the person so afflicted has important events, often in public, and the presence of such a "pimple" on the face would prove to be embarrassing. To many adolescents, such a condition is also emotionally disturbing. Also, if the acne condition is left untreated or the particular location of the acne manifestation is scratched or otherwise disturbed, the person is often left with a permanent skin scar or other skin disfigurements. Since the acne or similar skin condition may occur virtually simultaneously in closely adjacent or spaced apart locations on the skin and/or in short spans of time at various places on, for example, the face of the person, it is desired that there be a form of treatment that may also be applied simultaneously to many locations on the skin of the person.

For effective control of the acne or similar skin condition, it has long been desired to have a treatment for this condition that is also easy to apply to the affected area or areas, is relatively fast acting and comparatively inexpensive. The treatment must also have no deleterious surface effects and be safe and easy to apply to the skin and is peelable, removably adhesively connected to the skin and easy to both apply and remove from the skin when the treatment is complete.

Therefore, it has long been desired to have a treatment for acne or similar skin conditions that is comparatively easy to apply to the affected skin area, easy to remove from the affected skin area, is fast acting and is safe to handle and has no adverse surface effects.

Accordingly, it is an object of the present invention to provide a medicated patch for the rapid treatment of acne or similar skin conditions.

It is another object of the present invention to provide a medicated patch for the rapid treatment of acne or similar skin conditions which is easy to apply to and remove from the affected skin areas.

It is another object of the present invention to provide a medicated patch for the rapid treatment of acne or similar skin conditions which is adhesively retained on the surface of the skin.

It is yet another object of the present invention to provide a medicated patch for the rapid treatment of acne or similar skin conditions which is readily removable from the skin when the treatment is complete and has no deleterious surface effects.

It is another object of the present invention to provide a medicated patch for the rapid treatment of acne or similar skin conditions wherein a plurality of the pads containing the medication are available to the user in a convenient array in on a base and individual medicated pads may be removed from the base on which the pads are mounted without disturbing the remainder of the medicated pads mounted on the base.

SUMMARY OF THE INVENTION

The above and other objects of the present invention are; achieved, in a preferred embodiment thereof, by providing a base member such as a thin, flexible sheet of polypropylene which may be on the order of 0.5 to 1.0 mm thick. The base member is utilized as a member for carrying a plurality of the medicated pads which treat the acne or other skim condition. Thus, a plurality of pads containing the medication according to the principles of the present invention may, in preferred embodiments of the present invention, be installed upon the base member after the pads are fabricated.

The pads containing the medication are a multi-layer configuration and are fabricated by applying a first layer of peelable adhesive such as vinyl acetate to a first surface of a transport sheet. The transport sheet may be a thin, flexible sheet of polypropylene on the order of 0.1 to 0.5 mm thick. The adhesive is let dry for about 24 hours. When the adhesive is dry, a layer of the medication is applied to the layer of dry adhesive.

The medication is a homogeneous mixture. The homogeneous mixture is a mixture of about 1.0-2.0% salicylic acid, 70-90% vinyl acetate-2 (acrylic adhesive), 2.0-5.0% zinc oxide, 6.0-10% 1,2 propylene glycol and 1.0-3.0% polyvinylpyrrolidone (commonly called kollidon). The above percentages are by volume. The salicylic acid of the mixture of these ingredients is converted to nanomaterials by known nanotechnology techniques prior to the addition of the other ingredients to provide the medication mixture for use in the present invention. The medication mixture has a viscosity of about 6000 CPS. The mixture of the nanomaterial salicylic acid and the other ingredients of the medication is then stirred or otherwise agitated to provide a homogeneous mixture.

A thin layer of the homogeneous mixture of the medication mixture is applied to the dried first layer of adhesive on the transport sheet to provide a medication dose of about 0.2 gm on each of the ultimate pads and the layer of medication is allowed to dry for about 24 hours. When the medication layer is dry, a second, thin layer of peelable adhesive such as a vinyl acrylic adhesive is applied to the dry layer of medication and allowed to dry for about 24 hours.

A final outer thin layer of a peelable adhesive such as vinyl acrylic adhesive is then applied to the second surface of the transport sheet and allowed to dry for about 24 hours.

The transport sheet with the multilayers as above described is then cut into a plurality of pads, which may be on the order of about 15 mm in diameter, and the discs are placed on the base sheet in a preselected array such a linear array of two columns by five rows, though other arrangements of the pads on the transport sheet may be utilized as desired, by pressing the final, outer thin layer of adhesive on the second surface of the transport onto the base sheet.

In use, a pad is removed from the base sheet by peeling the outer layer of adhesive therefrom and the outer layer of the adhesive on the removed pad pressed onto the skin over the acne or other skin condition which is desired to treat. The transport sheet and the outer layer of adhesive are thereby raised to an elevated temperature of about the skin temperature. At the elevated temperature, the transport sheet and the outer thin peelable layer of adhesive are permeable to the medication and the medication and the medication flows through the first layer of adhesive, through the transport sheet and onto the skin at the location of the acne or other skin condition. Since the second layer of adhesive on the pad is exposed to the ambient temperature which is lower than the skin temperature, the medication does not flow therethrough. Thus, the transport sheet and the first layer of adhesive are selected such that at the expected range of skin temperatures each such material is permeable to the nanomaterial medication.

The pad is allowed to stay on the skin for about 10 to 12 hours as it has been found that most such acne conditions at the location of the pad are reduced or eliminated in such a short time period. The pad may then removed and safely disposed. This treatment may be repeated as often as desired depending on the acne or skin condition that is present since there are no adverse or deleterious effects from such repeated utilization of the present invention.

BRIEF DESCRIPTION OF THE DRAWING

The above and other embodiments of the present invention my be more fully understood from the following detailed description taken together with the accompanying drawing wherein similar reference characters refer to similar elements throughout and in which.

Figure 1:
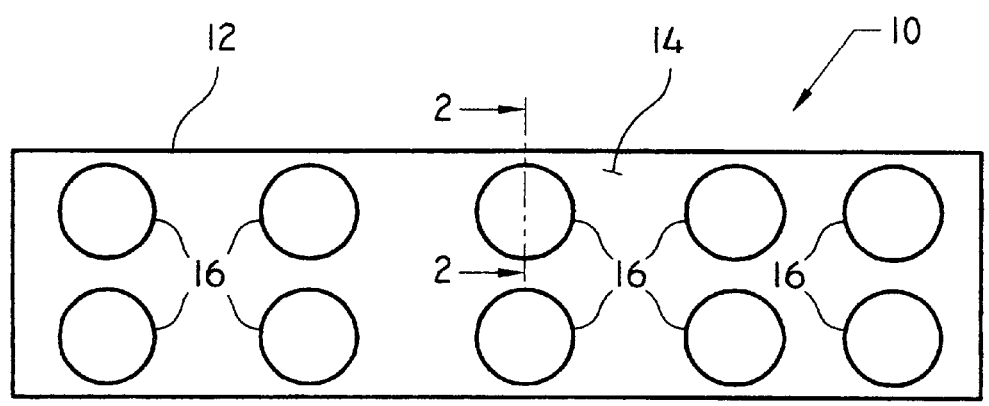
FIG. 1 illustrates a base member with a plurality of pads according to the present invention thereon.

Figure two illustrates a cross section of a medicated pad according to the principles of the present invention.

DESCRIPTION OF THE PREFERRED EMBODIMENTS

Referring now to the drawing, there is shown an embodiment generally designated 10 of a preferred form of the arrangement of the present invention. As shown thereon, there is provided a base sheet 12 having a first surface 14. A plurality of medicated pads 16 are removably mounted on the first surface 14 of the base sheet 12. The base sheet 12 may be a thin, flexible sheet of polypropylene having a thickness on the order of 0.5 to 1.0 mm. The purpose of the base sheet 12 is to provide a convenient carrier for the medicated pads 16. Therefore, the base sheet 12 may be made of any material upon which the medicated pads may be removably mounted as may be desired for particular applications.

Figure 2:
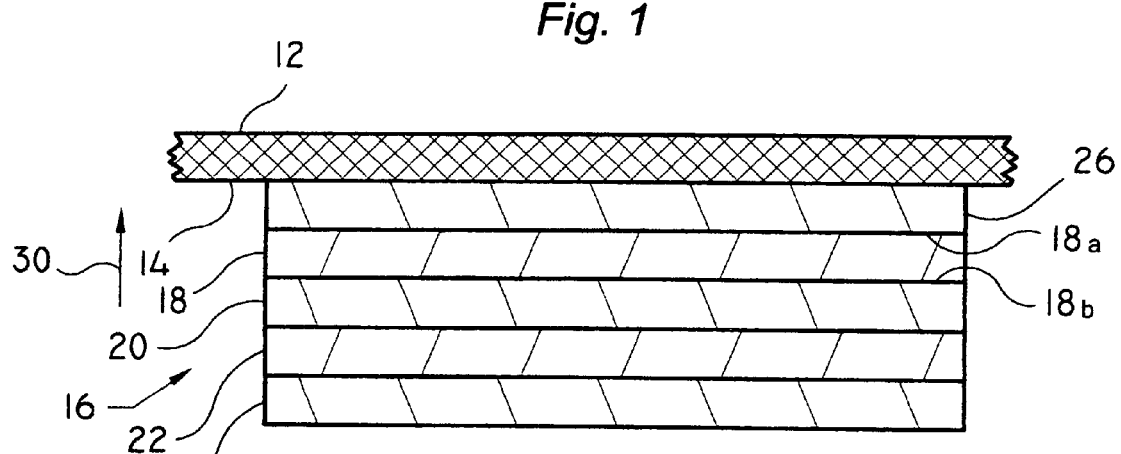

The medicated pads 16 are a multi layer pad as shown in FIG. 2. A transport sheet 18 of thin, flexible plastic such as polypropylene has a thickness of about 0.1 to 0.5 mm. The transport sheet 18 has a first surface 18a and a second surface 18b. A first layer of adhesive 20, such as vinyl acetate, is applied to the second surface 18b of the transport sheet 18. A layer of medication 22 is applied to the first layer of adhesive 20 and a second layer of adhesive 24, such as vinyl acetate, is applied to the layer of medication 22. A final, outer layer of adhesive 26 such as vinyl acetate is applied to the first surface 18a of the transport sheet 18. The outer layer of adhesive 26 is a peelable adhesive and is mounted on the first surface 14 of the base sheet 12. The outer layer of adhesive 26, the first layer of adhesive 20 and second layer of adhesive 24 may, as noted above, be made of vinyl acetate or any other desired material suitable for the purpose intended and having the desired properties as described herein. The transport sheet may be fabricated from materials other than polypropylene provided the material has the properties described herein.

As shown on FIG. 2, the medicated pads 16 have a preselected geometric shape and as illustrated, the preselected geometric shape in the embodiment 10 is circular, however, other geometric shapes may be selected as desired.

In use, a pad 16 is removed from the base sheet 12 and the outer layer of adhesive 26 is placed on the skin of the person in the region containing the skin condition, such as acne, that is to be treated. The outer layer of adhesive 26 allows the pad 16 to be removably attached to the skin and the pad 16 may remain on the skin for about 10 to 12 hours when it can then be removed. If the skin condition is not yet fully treated, the treatment may be repeated with a second pad.

The outer layer of adhesive 26, the transport sheet 18 and the first layer of adhesive 20 are raised to the temperature of the skin of the person on which the pad is placed and such temperature is generally elevated above the ambient temperature and at such elevated temperature these three layers 18, 20 and 26 of the pad 16 are permeable to the medication in the medicated layer 22. When the pad 16 is placed upon the skin of the person to treat the skin condition, the medication in the medicated layer 22 moves in the direction of the arrow 30 through the layers 26, 20 and the transport sheet 18 to the skin of the person.

The second layer of adhesive 24 remains at, substantially, the ambient temperature which is generally lower than the temperature of the skin of the person upon which the pad 16 is placed and the second layer of adhesive 24 acts as a barrier to the movement of the medication of the medication layer 22 in a direction opposite the direction of the arrow 30.

The medication in the preselected medication layer 22 is a mixture of preselected ingredients as shown in Table 1.

TABLE 1

| INGREDIENT | PERCENTAGE BY VOLUME |
| --- | --- |
| Salicyclic Acid (in nanomaterial condition) | 1.0-2.0% |
| Vinyl Acetate-2 (acrylic adhesive) | 70-90% |
| zinc oxide | 2.0-5.0%, |
| 1,2 propylene glycol | 6.0-10% |
| polyvinylpyrrolidone (commonly called kollidon) | 1.0-3.0% |

In preparing the medication layer 22, it has been found advantageous to employ the following steps after the salicylic acid has been converted to nanomaterial form:

1. Provide a mixture of the ingredients in Table 1;

3. Stir or other wise agitate the mixture to provide a homogeneous mixture. Thus, the layer 22 is a homogeneous mixture of the ingredients of Table 1.

In fabricating the pads 16, it has been found to be advantageous to employ the following steps:

1. Provide a transport sheet 18 of a thin, flexible sheet of polypropylene having a thickness of about 0.1 to 0.5 mm, though sheets of greater or less thickness may be utilized for particular applications;

2. Apply a first thin layer of adhesive 20 such as vinyl acetate to a second surface 18b of the transport sheet 18 and allow the first layer 20 of adhesive to dry for about 24 hours;

3. Apply a thin layer of the homogeneous medication mixture 22 to the dry first layer of adhesive 20 and the homogeneous medication mixture may have a thickness to provide a medication dosage on the order of 0.2 gm of medication on each of pads 16 as described below, though a greater or less dosage may be utilized for particular applications. The medication layer 22 is allowed to dry for about 24 hours.

4. Apply a thin second layer of adhesive 24 to the dry medication mixture 22 and the second layer of adhesive may be vinyl acetate and is allowed to dry for about 24 hours;

5. Apply a thin outer layer of peelable adhesive 26 such as vinyl acetate, to the first surface 18a of the transport sheet 18. Other materials than vinyl acetate may be utilized as the outer layer 26 of adhesive as required for particular applications provided the adhesive selected has the properties as described herein. The outer layer of adhesive 26 is allowed dry for about 24 hours;

6. When the outer layer of adhesive 26 is dry, the transport sheet with the above layers of material thereon may be cut into the individual pads such as the circular pads 16;

7. The second layer of adhesive 26 on each of the pads 16 is then pressed onto the base sheet 12 in the desired array so as to be removably mounted thereon.

It has been found that the vinyl acetate ingredient in the medication mixture as shown on Table 1 acts as a binder in maintaining the mixture in a homogeneous configuration in the pads 16 and the second layer of adhesive 24 acts as a barrier to prevent cold flow of the medication mixture 22 out of the pad 16.

This concludes the description of the present invention. As described above and as shown on the attached drawing, a medicated adhesive pad particularly adapted to the treatment of acne or similar skin disorders is provided which is relatively fast acting and may be removably placed on the skin of the person over the skin disorder to be treated. Such pad is comparatively fast acting and effective in treating the skin disorders, is comparatively inexpensive to manufacture is convenient to use and is generally free of deleterious side effects to the user thereof.

Although specific embodiments of the present invention have been described above with reference to the various Figures of the drawing, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

What is claimed is:

1. A medicated pad for treatment of preselected skin disorders comprising, in combination:
a base strip, said bases base strip comprising a thin flexible plastic sheet having a first surface and a second surface;
a plurality of medicated pads removably adhesively adhered to said base strip on said first surface thereof in a preselected array, each of said pads having a preselected geometric shape;
each of said medicated pads comprising a multi-layer pad comprising:
a thin, flexible transport plastic sheet having a first surface and a second surface;
a first layer of adhesive on said second surface of said thin, flexible transport plastic sheet;
a layer of preselected medication on said first layer of adhesive;
a second layer of adhesive on said layer of preselected medication; and
an outer layer of peelable adhesive on said first surface of said transport sheet configured for removable attachment to skin.

2. The medicated pad defined in claim 1 wherein:
said preselected geometric shape of said pads is circular;
said preselected array is a linear matrix comprising a plurality of aligned rows and a plurality of aligned columns.

3. The medicated pad defined in claim 1 wherein:
said preselected medication is a homogenous mixture of ingredients comprising salicylic acid in a nanomaterial form, vinyl acetate-2, zinc oxide, 1,2 propylene glycol and polyvinylpyrrolidone.

4. The medicated pad defined in claim 3 wherein:
said preselected medication has a dosage on each of said pads on the order of 0.2 gm.

5. The medicated pad defined in claim 2 wherein:
each of said pads is on the order of one 15 mm in diameter.

6. The medicated pad defined in claim 4 wherein:
the percentage by volume of said homogenous mixture of ingredients is:
1.0 to 2.0% nanoparticle salicylic acid, 70-90% vinyl acetate-2, 2.0 to 5.0% zinc oxide, 6.0 to 10.0% 1,2 propylene glycol and 1.0 to 3.0% polyvinylpyrrolidone.

7. The medicated pad defined in claim 6 wherein:
said thin, flexible transport plastic sheet, said first layer of adhesive and said outer layer of peelable adhesive are each permeable to said preselected medication for the temperature of said preselected medication at an elevated temperature greater than the ambient temperature whereby the preselected medication flows therethrough at such elevated temperature;
said second layer of adhesive is non-permeable to said medication mixture at temperatures lower than said elevated temperature.

8. A medicated pad for treating acne comprising:
a thin, flexible transport plastic sheet having a first surface and a second surface;
a first layer of adhesive on said second surface of said thin, flexible transport plastic sheet;
a layer of preselected medication on said first layer of adhesive;
a second layer of adhesive on said layer of preselected medication;
an outer layer of peelable adhesive on said second first surface of said transport sheet configured for removable attachment to skin.

9. The medicated pad defined in claim 8 wherein:
said preselected medication is a homogeneous mixture of:
1.0 to 2.0% nanomaterial salicylic acid, 70-90% vinyl acetate-2, 2.0 to5.0%, zinc oxide, 6.0 to 10.0% 1,2 propylene glycol and 1.0 to 3.0% polyvinylpyrrolidone, wherein the percentages are percentage by volume.

10. The medicated pad defined in claim 9 and further comprising:
a base sheet comprising a thin, flexible sheet of polypropylene on said outer layer of peelable adhesive; and,
said outer layer of peelable adhesive is removable attached to said base sheet.

11. The medicated pad defined in claim 10 wherein:
said thin, flexible transport plastic sheet, said outer layer of peelable adhesive and said first layer of adhesive are permeable to said preselected medication for said second layer of adhesive removably mounted on a person in regions containing acne.

12. The medicated pad defined in claim 11 wherein:
said layer of preselected medication provides a dosage of about 0.2 grams on each of said pads.

13. A method of making a medicated adhesive pad for treating a skin disorder condition on a person comprising the steps of:
   a. providing a transport sheet of a thin, flexible sheet of polypropylene having a thickness of about 0.1 to 0.5 mm, said transport sheet having a first surface and a second surface;
   b. applying a first thin layer of adhesive to a second surface of the transport sheet and allowing the first layer of adhesive to dry for about 24 hours;
   c. applying a thin layer of a homogeneous medication mixture to the first thin layer of adhesive after said first thin layer of adhesive is dry and the homogeneous medication mixture may have a thickness to provide a medication dosage of 0.2 gm of medication, and allowing the thin layer of homogeneous medication layer mixture to dry for about 24 hours;
   d. applying a thin second layer of adhesive to the dry thin layer of homogeneous medication mixture after the thin layer of homogeneous medication mixture is dry and allowing the thin second layer of adhesive to dry for about 24 hours;
   e. applying a thin outer layer of peelable adhesive to said first surface of the transport sheet configured for removable attachment to skin and allowing the outer layer of peelable adhesive to dry for about 24 hours;
   f. after the outer layer of peelable adhesive is dry, cutting the transport sheet with the layers of the first thin layer of adhesive, the thin layer of a homogeneous medication mixture, the thin second layer of adhesive and the thin outer layer of peelable adhesive thereon into the individual pads having a preselected geometrical shape;
   g. providing a base sheet of polypropylene;
   h. pressing the thin outer layer of peelable adhesive on each of the pads onto the base sheet of polypropylene in a preselected array so as to be removably mounted thereon.

14. The method defined in claim 13 wherein:
each of the steps of allowing each of the first thin layer of adhesive, the thin second layer of adhesive, the thin outer layer of peelable adhesive and the thin layer of homogeneous medication mixture to dry is on the order of 24 hours.

15. The method defined in claim 14 wherein:
each of said first thin layer of adhesive, said thin second layer of adhesive and said outer layer of peelable adhesive is vinyl acetate.

16. The method defined in claim 15 and further comprising the steps of:
   a. removing a pad from said base sheet of polypropylene to provide a removed pad;
   b. applying the removed pad to the skin of a person to cover a skin disorder by pressing the outer layer of peelable adhesive onto the skin;
   c. allowing the removed pad to remain on the person for a time period of about 10 to 12 hours.

17. The method defined in claim 16 wherein:
said thin layer of a homogeneous medication mixture provides a dosage of said thin layer of medication mixture on said removed pad of about 0.2 gm.

\* \* \* \* \*